United States Patent [19]

Lindow et al.

[11] Patent Number: 5,757,988
[45] Date of Patent: May 26, 1998

[54] OPTICAL FIBER SENSOR UTILIZING A SWELLABLE DETECTOR MATERIAL

[75] Inventors: James T. Lindow, Saratoga; Dean T. Mack, Los Altos; Edward R. McCourt, Jr., Palo Alto, all of Calif.

[73] Assignee: Mark Products, Inc., Sunnyvale, Calif.

[21] Appl. No.: 760,400

[22] Filed: Dec. 4, 1996

Related U.S. Application Data

[60] Provisional application No. 60/008,222 Dec. 5, 1995.
[51] Int. Cl.[6] .................................................. G02B 6/00
[52] U.S. Cl. ........................................ 385/13; 250/227.16
[58] Field of Search .............................. 385/13; 250/227.16

[56] References Cited

U.S. PATENT DOCUMENTS

| | | |
|---|---|---|
| 4,590,462 | 5/1986 | Moorehead . |
| 4,596,443 | 6/1986 | Diemeer et al. . |
| 5,220,160 | 6/1993 | Sargoytchev . |
| 5,243,670 | 9/1993 | Bonicel . |
| 5,378,889 | 1/1995 | Lawrence . |
| 5,430,815 | 7/1995 | Shen et al. . |

FOREIGN PATENT DOCUMENTS 63-228105  9/1988  Japan .

*Primary Examiner*—Frank G. Font
*Assistant Examiner*—Amanda Merlimo
*Attorney, Agent, or Firm*—Robert S. Kelly

[57] ABSTRACT

An optical fiber sensor for inducing a microbend in an optical fiber in the presence of a detectable fluid such as water includes a chamber with an expansible block located therein. When water enters the chamber, the block expands in a particular direction to move a pusher bar which, in turn, moves a puller wire to bend the fiber at a location remote from the chamber. A gap may initially be provided between the expansible block and the pusher bar so that the presence of water vapor within the chamber will not move the pusher bar but the presence of liquid water will.

21 Claims, 2 Drawing Sheets

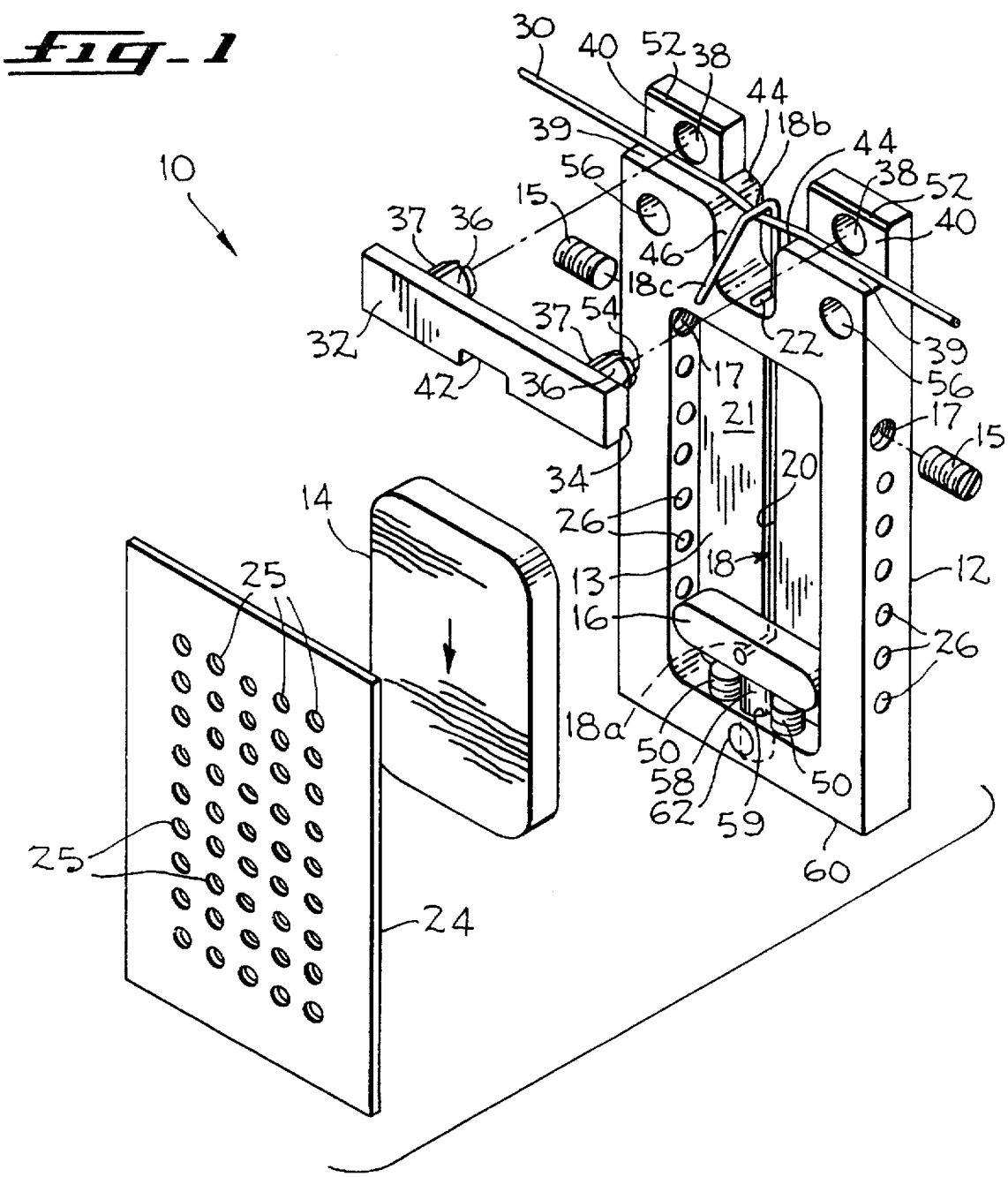
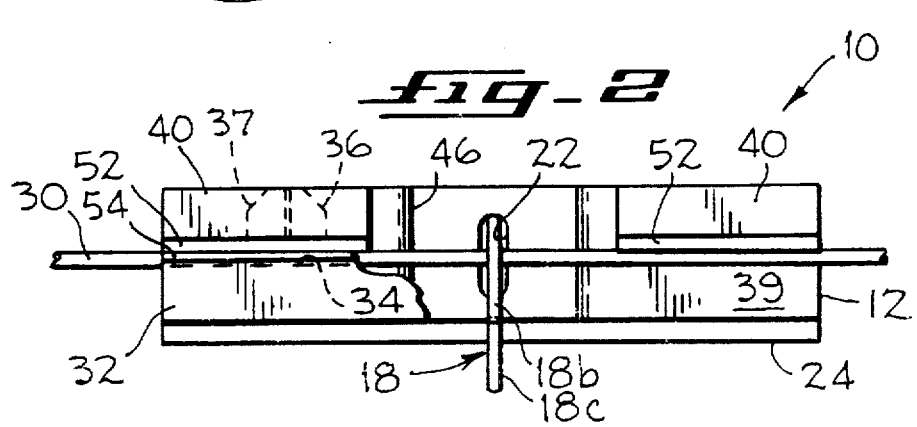

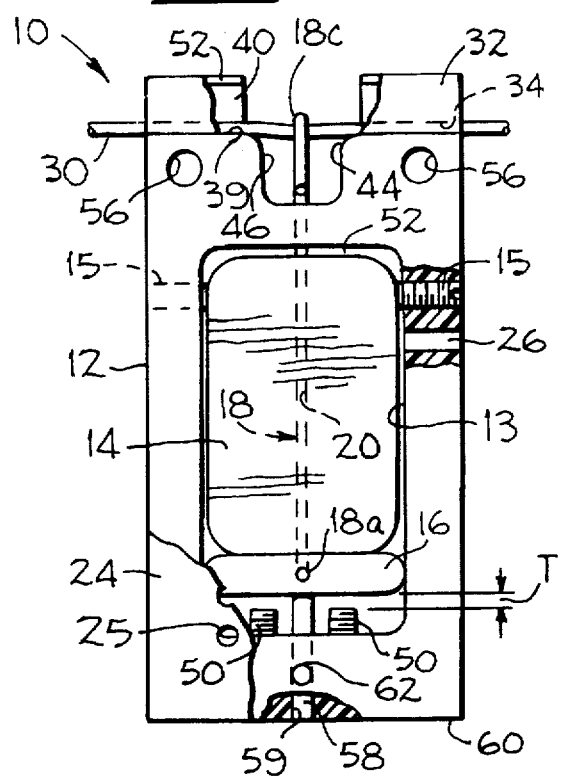
fig_3
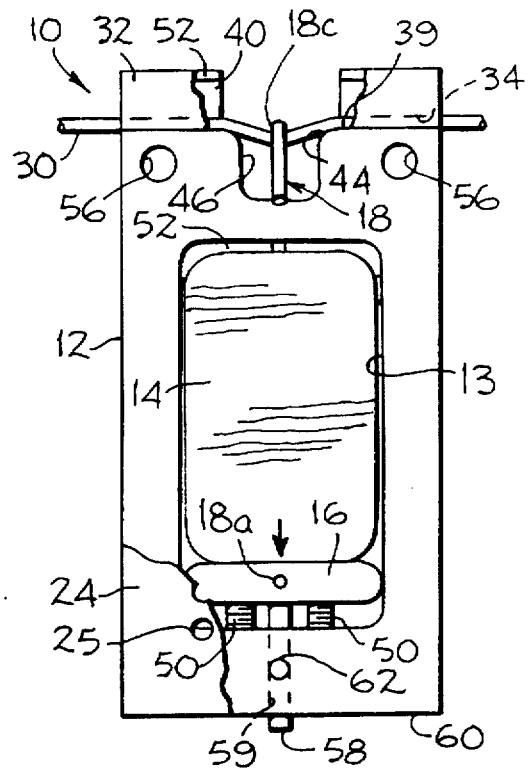
fig_4
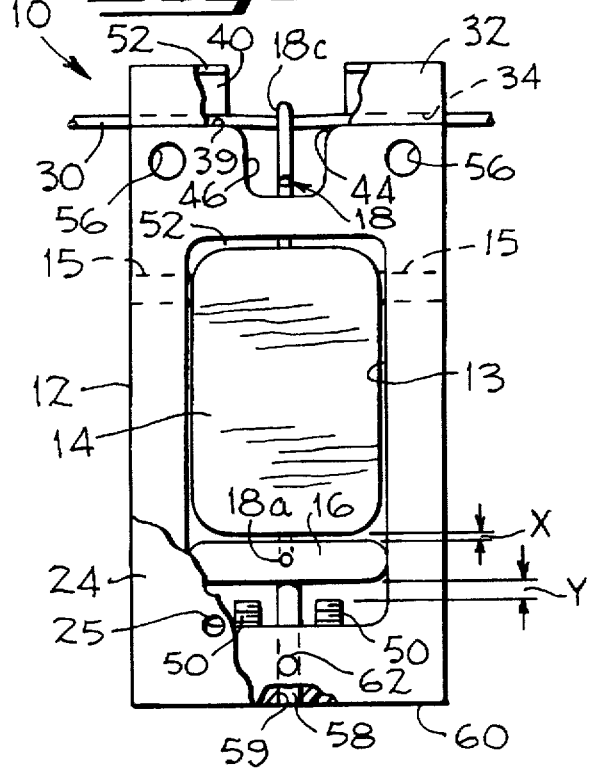
fig_5
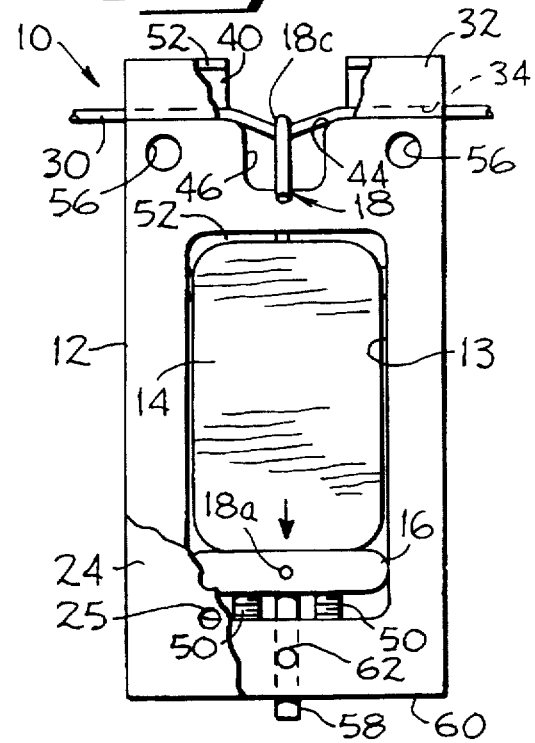
fig_6

OPTICAL FIBER SENSOR UTILIZING A SWELLABLE DETECTOR MATERIAL

REFERENCE TO PRIOR APPLICATION

This application claims the benefit of U.S. Provisional Application No. 60/008,222, filed Dec. 5, 1995 and entitled OPTICAL FIBER SENSOR UTILIZING A SWELLABLE DETECTOR MATERIAL.

BACKGROUND OF THE INVENTION

1. Field of the Invention

The present invention pertains to optical fiber sensors for sensing fluid (gaseous or liquid) substances, such as water vapor or water, and more particularly, it pertains to optical fiber sensors which utilize a swellable material in the presence of the fluid substance to be detected which swelling is arranged to mechanically cause a microbending in the optical fiber that can readily be detected and analyzed by conventional monitoring devices.

2. Description of the Prior Art

Optical fiber sensors for sensing the presence of a particular fluid substance such as water vapor, water, petrochemicals, etc., are well-known in the prior art. The presence of the fluid substance at a remote location, such as a buried telecommunications box, is sensed by a carefully chosen substance which is caused to thereby swell and mechanically create a stress in or, particularly, a microbending in the optical fiber which condition can then be readily detected by the attenuation in the signal transmitted by the fiber or by optical time domain reflectometer (OTDR) circuitry which reacts to the signal loss at the microbend and accurately pinpoints its location along the length of the optical fiber.

Prior United States patents which disclose the use of a fluid sensor employing the microbending of an optical fiber include the Bonicel U.S. Pat. No. 5,243,670 wherein the presence of moisture is detected within a closed chamber; U.S. Pat. No. 4,596,443 to Diemeer et al disclosing a fiberoptic sensor for detecting the presence of a liquid such as ground water within a multiconductor cable; U.S. Pat. No. 5,378,889 to Lawrence disclosing a fiberoptic sensor for the detection of hydrocarbon fuels; and U.S. Pat. No. 5,430,815 to Shen et al which discloses an optical fiber sensor for detecting the presence of water wherein a swellable material forces the optical fiber to be bent about a curved mandrel. Optical fiber sensors utilizing the microbending of the fiber for detection purposes have also been used to detect shockwaves as shown, for example, in the prior patent to Sargoytchev, U.S. Pat. No. 5,220,160.

While in the foregoing patents the swellable material directly impacts a force to the fiberoptic cable, the location for detecting the presence of particular fluid substance may be separated from the location of the fiber attenuation imparting means so as to prevent any contact therebetween with a mechanical connection being provided to impart a bending to the fiber upon the remote sensing of the fluid substance as shown, for example, in the U.S. Pat. No. 4,590,462 to Moorehead disclosing an optical fiber sensor for the detection of hydrocarbons.

A particular industry which has utilized optical fiber sensors in the past is the telecommunications industry wherein fiberoptic splice cases are used at remote locations as junctions or splice points for the fiberoptic cables. Typically, these splice cases are buried underground and are thereby subject to water intrusion if the cases should leak. Since such leakage can have significant consequences on the accuracy and reliability on the information communicated over the fiberoptic cables, it is imperative that the presence of water in the splice case be communicated to some remote operating point as soon as possible. Furthermore, it may be desirable to distinguish between the presence of free water and water vapor and to readily distinguish between the two.

SUMMARY OF THE INVENTION

In accordance with the present invention an optical fiber sensor is provided which utilizes the well-known technique of providing a swellable or expansible material which expands in the presence of a particular gaseous or liquid fluid to be detected and which expansion causes a microbending of an optical fiber which can be sensed at a remote location as, for example, by typical OTDR equipment.

With the present invention, a chamber is provided for the expansible material and a mechanical connection is made between a pusher bar arranged to move with the expansible material and the optical fiber which is located in a separate, spaced location and not directly in contact with the expansible material. The fiber is arranged to be deflected into a cavity when the expansible material is caused to swell with three support surfaces of controlled geometry for the fiber being provided at the microbend, such surfaces including the member pushing the fiber into the cavity as well as the two spaced support surfaces for the fiber at the edges of the cavity. In this way, the deflection will be precisely predetermined under a given degree of expansion of the swellable member so that the signal provided by the microbending of the fiber can be readily and correctly analyzed and processed to give an appropriate determination of the quantity and/or nature of the fluid being detected.

In the preferred embodiment of the invention, the optical fiber sensor is used to detect the presence of either water vapor or liquid water within the detection chamber. In order to distinguish between the presence of water vapor and the presence of free standing water, the pusher bar may be spaced from the expansible material by a predetermined amount so that the accumulation of water vapor within the chamber will not provide any bending of the optical fiber. It will only be after the presence of a significantly larger amount of water, i.e., where there is water in liquid form, that the pusher bar will be moved sufficiently to bend the optical fiber and thereby provide a detectable signal condition. Obviously, for a given size and shape of expansible material the amount of permissible swelling of material due to water vapor alone may be predetermined and the pusher bar spacing may be set so that the presence of water vapor alone will not create bending of the fiber. Alternatively, means may be provided to prevent the force exerted by the engagement of the pusher bar by expansible material from moving the bar in the presence of water vapor alone in the detection chamber conditions under which the device is designed to be used.

BRIEF DESCRIPTION OF THE DRAWINGS

FIG. 1 is an exploded view of the optical fiber sensor of the present invention.

FIG. 2 is an enlarged top plan view of the assembled optical fiber sensor of FIG. 1 with a portion thereof being broken away for the purposes of illustration.

FIG. 3 is a front elevation of the optical fiber sensor of FIG. 1 with portions thereof being broken away and particularly illustrating the device in the absence of the detectable fluid.

FIG. 4 is a front elevation of the optical fiber sensor of FIG. 1 similar to FIG. 3 but illustrating the condition of the sensor upon the intrusion of the detectable fluid into the sensor chamber and the resultant microbending of the optical fiber.

FIG. 5 is a front elevation view of a second embodiment of the present invention similar to the first embodiment of the invention, as shown in FIG. 3, but with the pusher bar thereof being initially spaced from the swellable material so as to permit the accumulation of a certain amount of water vapor in the sensor chamber without causing any consequent bending of the optical fiber and with FIG. 5 showing the initial (no water vapor or water) condition of the sensor.

FIG. 6 is a front elevation view of the second embodiment of the present invention similar to FIG. 5 but with the presence of free water in the sensor chamber causing sufficient expansion of the swellable material far enough to create microbending of the optical fiber.

DESCRIPTION OF PREFERRED EMBODIMENTS

The components of the optical fiber sensor 10 of the present invention are shown in exploded form in FIG. 1. The sensor is designed to utilize the well-known phenomenon of measurable light loss or reflection from a selectively bent optical fiber 30 to indicate the presence of a particular fluid substance. The fluid to be detected may be a liquid or a gas, e.g., water, or water vapor, or hydrocarbons in either liquid or vapor form. In order to provide for the basic detection process a swellable or expansible material in rectangular block form 14 (FIG. 1) is provided, which block is adapted to predictably swell in at least one of its dimensions in the presence of the detectable fluid and which swelling is designed to cause the bending of the fiber 30 in a controlled manner to provide the appropriate signal to conventional monitoring equipment such as an OTDR (not shown) operating from a distant location along the length of the fiber.

While the optical sensor 10 of the present invention may thus be used for detecting various types of fluids in various types of environments, in the embodiments of the invention specifically disclosed herein, the sensor 10 is particularly intended to be utilized in connection with the monitoring of telecommunications fiber optic splice cases conventionally used in the telecommunications industry at locations such as junctions or splice points for fiber optic cables. Typically, the splice cases are buried underground and are thereby subject to water and/or water vapor intrusion if, for any reason, the seals should fail. Since such leakage into the cases can have significant consequences on the accuracy and reliability of the information communicated over the fiber optic cables, it is imperative that the presence of water in the splice case can be communicated to some remote operating point as soon as possible. The sensor of the present invention is designed to accomplish that function.

In choosing the material for the sweller block 14, a suitable material should be used which will swell substantially and reliably in the presence of free water, as for example, a polyvinyl fluoride or a polymer such as a crosslinked polyvinyl alcohol or other polymers as discussed in prior U.S. Pat. No. 5,015,843 to Seitzet al. In the present invention, however, the material chosen is a balsa wood with the grain being provided crosswise to the major longitudinal dimension of the block so that expansion due to water or water vapor intake will primarily occur in the direction of the arrow (FIG. 1). Thus, the major swelling expansion of the balsa wood block 14 occurs in the vertical direction (as seen in FIG. 1) with the wood grain extending as indicated, in the horizontal direction.

As can be seen from FIG. 1, the sensor 10 is comprised of a generally rectangularly shaped, recessed body member 12 provided with a rectangular cavity 13 therein in which is adapted to be closely fitted the sweller block 14. As can be seen in the assembled views of FIGS. 3 and 4, the vertical sides of block 14 are spaced slightly from the sides of the cavity 13 to permit slight expansion of the block in the direction of the wood grain and to prevent any binding of the block in the cavity so as to retard its swelling movement in the longitudinal (vertical) direction. The top of the sweller block 14 is positioned at or near the upper end (FIG. 1) of the cavity 13, and the upper end of the sweller block is tightly fixed in position by a pair of set screws 15 which are screwed into threaded apertures 17 in the side of the body member so that the very upper portion of the block 14 only will be tightly held in place. It will be recognized therefore that the largest swelling of the block 14 within the cavity 13 will occur in the longitudinal direction of the body, i.e., in the direction of the arrow shown in FIG. 1. A pusher bar 16 of a rigid material is securely fastened, as by a suitable adhesive, to the lower or expanding end of the sweller block 14 so as to move downwardly therewith when the presence of water or water vapor in cavity 13 causes the sweller block to expand. A puller wire 18 is inserted into and securely attached to the pusher bar 16 at its lower end 18a thereof and is arranged to slide along a groove 20 in the flat rear wall 21 of cavity 13 when the pusher bar 16 is moved. The upper end of the puller wire 18 passes through a slot 22 at the upper end of body member 12 to a position outside of the cavity 13 and above the fiber 30. The upper end of the puller wire 18 is formed with a right angle section 18b which lies above and in contact with the fiber 30 and a forwardly and downwardly bent section 18c serving to enclose the fiber. It will therefore be seen that as the pusher bar 16 is lowered under the impetus of the expanding sweller block 14, the puller wire 18 will act through section 18b thereof to pull downwardly on the fiber causing it to bend and creating the detectable light loss and/or reflection in the fiber for the conventional monitoring devices such as an OTDR previously mentioned.

The sweller block 14 and the pusher bar 16 are both captured within the body cavity 13 by means of a cover plate 24 which is adapted to be bonded or otherwise securely fastened to the peripheral face of the body member 12 above the cavity 13 thereof. It will be appreciated that the depth of the cavity 13 is slightly greater than the thickness of the sweller block 14 so that when the cover plate is fastened to enclose the cavity, some slight swelling of the block in its narrow transverse direction can occur without binding the block in the cavity or retarding the swelling movement in the vertical (FIG. 1) direction. The cover plate 24 is provided with a plurality of holes 25 to allow free inflow of water or water vapor to the various surfaces of the sweller block 14. As can be seen in FIG. 1, each of the side walls of the body member 12 is provided with a plurality of apertures 26 leading into the cavity 13 to further provide for the free flow of water or water vapor into the cavity and to the sweller block 14. Thus, any water that is present about the sensor will be allowed to flow freely into the cavity and about the sweller member 14 thereby causing its expansion primarily in its longitudinal direction, i.e., downwardly toward the open end of the cavity.

In order to permit the fiber 30 to be readily attached to (or detached from) the optical fiber sensor 10 of the present invention, a removable capture block 32 (FIG. 1) is provided. The capture block is formed of a generally rectangular shape and includes two spaced pairs of flexible projections 36, 37 which are adapted to be pressed into cylindrical apertures 38 in a pair of spaced and upwardly projecting flanges 40 at the upper end of the body member 12. A notch 34 (FIG. 1) is provided along the lower and inner face of the capture block so as to provide a passage just large enough for the capture of the fiber 30 along a pair of flat ledges 39 formed at the upper end of body member 12. Thus, with the capture block removed from the body, as shown in the exploded view of FIG. 1, the fiber may be slipped under the end 18c of the puller wire 18 so as to rest on the ledges 39 up against flanges 40. The projections 36, 37 of capture block 32 are then pressed into the apertures 38 with the notch 34 therein securing the fiber and preventing its lateral movement but permitting free longitudinal movement thereof when it is pulled by puller wire 18 and thus providing a rapidly and replaceable snap-fit connection. It will be seen, therefore, that the optical fiber 30 can be removed and replaced in the sensor 10 without requiring the threading of an end of the fiber through the body of the sensor. As can further be seen in FIG. 1, the bottom of the capture block is provided with a notch 42 to permit the projection of and free movement of the enclosing end 18c of the puller wire.

An important aspect of present invention is the use of a controlled geometry in the sensor to precisely define the manner in which the optical fiber 30 is bent from its initial position (no presence of water or other detectable fluid) to a final (maximum) position limiting the microbending of the fiber so that permanent damage thereto does not occur. For this latter purpose, it will be noted that a pair of set screws are adjustably threaded into the bottom wall of the body member 12 forming the bottom of the cavity 13, and, as particularly seen in FIGS. 3 and 4, such set screws are designed to abut against the bottom of the pusher bar 16 after the sweller block 14 has expanded by a maximum distance T. Obviously, such distance T can be adjusted for different operating conditions by raising or lowering the screws 50 within the body member 12 or by adjusting the upper fixed position of the sweller block 14 (it being noted that a small space 52 at the upper end of the cavity 13 is provided for this latter purpose).

A second aspect of the controlled geometry feature is to relatively tightly enclose the fiber 30 by means of the notch 34 as aforedescribed but yet permit free sliding longitudinal travel of the fiber as it is pulled along the ledges 39 during the bending operation as shown by the fiber movement indicated between FIGS. 3 and 4. As the fiber is bent downwardly, the fiber is pulled over the ledges 39 around a pair of surfaces 44 curved about a uniform radius and into a cavity 46 in the body member. The smoothly curved shape of the surfaces 44 is designed to minimize the reflective losses and to produce splice-like microbending losses in the fiber without damaging or permanently altering the optical transmission characteristics of the fiber. The size of the puller wire 18 is also carefully chosen so as not to create undue stress at its contact surface with the fiber in the section 18b of the puller wire. In the present instance, utilizing a conventional single mode telephone communication fiber with a common size of 125/9 (about 250 microns in diameter including the buffer layer thereof) a size of puller wire of 0.014 inches in diameter was chosen. The smooth corners 44 about which the fiber is bent are arcs with a radius of about 0.0625 inches. With this three support surface (44-18b-44) geometrical arrangement for the fiber at the deflection cavity 46, the sensor 10 of the present invention can be used to produce signal losses in the fiber 30 from about 0.05 db to about 2.5 db at the typical telecommunications wavelengths of from about 1300 nanometers to about 1650 nanometers and with the maximum fiber deflection distance T (FIG. 3) being from about 20 mils to about 50 mils.

It will further be noted that the upper edges of the flanges 40 of body member 12 are beveled at 52 to mate with a similarly beveled edge 54 on the upper and inner edge of capture block 32 (see FIG. 2) so that the capture block may be readily separated when necessary from the body member 12 of the sensor by means of a fingernail or suitable tool to insert or remove the optical fiber 30 therefrom. The upper portion of the body member 12 is also provided with a pair of apertures 56 extending therethrough (FIG. 1) to permit the sensor 10 of the present invention to be securely mounted, as by screws or other fastening devices, if such should be necessary.

Finally, it will be noted that the pusher bar 16 is provided with a downwardly extending stem 58 which is adapted to be loosely engaged in an aperture 59 extending through the bottom wall of the body member 12 from cavity 13 thereof to the outer lower face 60 thereof, as particularly seen in FIG. 3. In the initial, unbiased position of the sensor, the lower end of the stem 58 will extend just to the lower face 60 of the sensor. However, as seen in FIG. 4, when the sweller block 14 expands downwardly (in the direction of the arrow) the stem 58 likewise projects downwardly and out of the body member 12 so as to provide a clear mechanical or visual signal that water or other detectable fluid has penetrated into the sweller block. An aperture 62 extends from the face of the body member 12 and into the passage 59 therein so that when the device is assembled, some wax or other temporary adhesive may be inserted through aperture 62 and about the stem 58 in the passage 59 so as to hold the components of the device together in a fixed position and prevent any mechanical vibration or other shocks from disturbing the pre-set positions of the components. However, such wax or other temporary adhesive means are not sufficient to prevent the bond from being broken when the sweller block expands in the presence of the detectable fluid (water) whereby the stem 58 can then be readily pushed out of the body member 12 as shown in FIG. 4.

A second embodiment of the invention is shown in FIGS. 5 and 6. The various components of the sensor of FIGS. 5 and 6 are generally the same as the previously described embodiment 10 of the invention and like numbers will be used in describing the operation of the device of FIGS. 5 and 6. As with the originally described embodiment of the invention as shown in FIGS. 3 and 4, FIG. 5 will be seen to show the initial position of the optic fiber 30 in the absence of any of the fluid to be detected, e.g., water, in the cavity 13, and FIG. 6 shows the fully bent position of the fiber 30 under maximum microbending due to the intrusion of fluid into and the consequent swelling of the sweller block 14. The embodiment of the invention shown in FIGS. 5 and 6 is specifically designed for the detection of water, and it is designed to operate so that the presence of water vapor alone will not create a microbending of fiber 30 so as to provide a detectable signal. In order to accomplish this, the pusher bar 16 is not securely attached to the sweller block 14 of balsa wood as in the previously described embodiment. Instead, the upper face of the pusher bar is initially spaced from the bottom face of sweller block 14 by a distance X (FIG. 5) whereby the presence of water vapor in the cavity 13 may cause longitudinal swelling of block 14 throughout such distance X without any movement being imparted to the puller wire 18 so as to create a detectable signal from the sensor. It is only after the sweller block 14 has longitudinally expanded past the distance X and into the dimension Y (as shown in FIG. 5) that the detectable microbending of fiber 30 will occur so as to provide a signal. As with the previously described embodiment, adjustable set screws 50 are provided in the bottom wall of the body member 12 so as to limit the maximum displacement of the puller wire 18 to the fixed distance Y.

In the embodiment of the invention shown in FIGS. 5 and 6, the use of the wax or other temporary adhesive pumped through the aperture 62 and into the passage 59 is of greater importance than in the first described embodiment. Thus, the adhesive secures the piston 58 in the initial setup of the sensor as shown in FIG. 5; however, as with the first embodiment, when water causes the balsa block 14 to expand into the distance Y, the adhesive is readily broken allowing the stem 58 to project from the lower face 60 of the sensor and thereby provide a mechanical signal which will readily be detected by one inspecting the sensor. The remaining wax or other adhesive within the passage 59 through the body member will, however, provide a good frictional fit for the stem 58 so that even if the water in the cavity 13 dries out to cause the sweller block 14 to shrink back to or near to its initial position, the stem 58 will remain in its position protruding from the sensor to provide a clear indication that water leakage had occurred at some time and that possible damage to the fiber optics may have also occurred. It will also be clear that the pusher bar 16 to which the stem is attached will also remain in its moved position so that the detectable bent condition if the fiber 30 will remain.

Alternatively, in the FIG. 5 embodiment of the invention, a compressible foam rubber-like material may be inserted into the space X between the pusher bar 16 and the bottom of the sweller block 14. With such an arrangement, the sweller block will expand through a certain distance before the force exerted through the foam rubber-like material will break the adhesive on the stem 58 to create a condition so that the force exerted on the pusher bar 16 by the sweller block will cause the pusher bar 16 (and the puller wire 18 attached thereto) to move to deflect the optical fiber 30 in the manner hereinbefore set forth.

In the foregoing two described embodiments of the invention, the sweller block 14 material was specifically described as a balsa wood with the grain thereof extending at right angles to the primary direction of elongation of the block. A suitable alternative material to balsa wood is a compressed cellulose sponge material which may be sized and attached to the indicated components of the sensor as shown in FIGS. 3–6 and as hereinbefore described.

While the foregoing description was particularly directed to the detection of water in a normally dry environment, such as in a fiber optic splice case, as explained previously the invention may be used to detect other liquids or gases in wholly different environments. For example, if it is desired to detect hydrocarbons (e.g., gasoline) in a water environment, a red silicon rubber material may be used for the sweller block material 14, the rubber swelling in the presence of hydrocarbons but not water.

Although the best modes contemplated for carrying out the present invention have been herein shown and described, it will be apparent that other modifications and variations may be made without departing from what is regarded to be the subject matter of the invention.

What is claimed is:

1. An optical fiber sensor for detecting the presence of a particular gaseous or liquid substance comprising means for providing a track for receiving an optical fiber along a predetermined path including a cavity therein to permit the fiber to be deflected out of said predetermined path, means defining a chamber spaced from said predetermined path, said chamber being provided with sufficient openings to permit the flow of said gaseous or liquid substance within said chamber, a block of expansible material positioned within said chamber with said material being subject to expansion in the presence of said particular gaseous or liquid substance, said chamber and block of material being relatively dimensioned to as to permit the expansion of the block of material in a particular direction within the chamber, a pusher member positioned to move with said block of material as it expands in said direction, said pusher member including a deflecting element arranged in contact with said fiber for causing said fiber to be deflected into said cavity when the block of material expands in the presence of said particular gaseous or liquid substance, and a stop positioned in said chamber in a location to engage the pusher member to limit the movement of the pusher member to a predetermined amount in order to prevent damage to or excessive bending of the optical fiber.

2. An optical fiber sensor according to claim 1 wherein said means for providing a track and said deflecting element provide three spaced support surfaces of curvilinear shape for the fiber adjacent said cavity with each of such surfaces being provided with a carefully controlled geometry so that the fiber will be bent in a predetermined manner for a given length of movement of the deflecting element.

3. An optical fiber sensor according to claim 1 wherein said chamber has two ends with said block being fixed in position substantially at one end of the chamber and being expandable in the presence of said substance into the other end of the chamber.

4. An optical fiber sensor according to claim 1 including means for adjustably mounting said stop in said chamber so that the limit to the pusher member movement can be precisely set for different operating conditions.

5. An optical fiber sensor according to claim 1 including means for preventing the pusher member from returning to its initial position in the chamber after it has been moved therefrom by the expansion of the block of expansible material even during subsequent contraction of the block.

6. An optical fiber sensor for detecting the presence of a particular gaseous or liquid substance comprising means for providing a track for receiving an optical fiber along a predetermined path including a cavity therein to permit the fiber to be deflected out of said predetermined path, means defining a chamber spaced from said predetermined path, said chamber being provided with sufficient openings to permit the flow of said gaseous or liquid substance within said chamber, a block of expansible material positioned within said chamber with said material being subject to expansion in the presence of said particular gaseous or liquid substance, said chamber and block of material being relatively dimensioned so as to permit the expansion of the block of material in a particular direction within the chamber, a pusher member positioned to move with said block of material as it expands in said direction, said pusher member including a deflecting element arranged in contact with said fiber for causing said fiber to be deflected into said cavity when the block of material expands in the presence of said particular gaseous or liquid substance, said pusher member being adapted to be engaged by said block during the expansion thereof, and said deflecting element comprising a puller wire attached to said pusher member to move therewith, said puller wire being positioned so as to engage said fiber to pull the fiber along the longitudinal axis of the fiber and cause the fiber to bend into said cavity when the block of material expands.

7. An optical fiber sensor according to claim 6 wherein said pusher member is positioned so as to engage said block of material in the absence of said particular gaseous or liquid substance in said chamber.

8. An optical fiber sensor according to claim 6 wherein said pusher member is spaced from said block of material by a predetermined amount in the absence of said particular gaseous or liquid substance in said chamber.

9. An optical fiber sensor for detecting the presence of a particular gaseous or liquid substance comprising means for providing a track for receiving an optical fiber along a predetermined path including a cavity therein to permit the fiber to be deflected out of said predetermined path, means defining a chamber spaced from said predetermined path, said chamber being provided with sufficient openings to permit the flow of said gaseous or liquid substance within said chamber, a block of expansible material positioned within said chamber with said material being subject to expansion in the presence of said particular gaseous or liquid substance, said chamber and block of material being relatively dimensioned so as to permit the expansion of the block of material in a particular direction within the chamber, a pusher member positioned to move with said block of material as it expands in said direction, said pusher member including a deflecting element arranged in contact with said fiber for causing said fiber to be deflected into said cavity when the block of material expands in the presence of said particular gaseous or liquid substance, said means for providing a track and said deflecting element providing three spaced support surfaces of curvilinear shape for the fiber adjacent said cavity with each of such surfaces being provided with a carefully controlled geometry so that the fiber will be bent in a predetermined manner for a given length of movement of the deflecting element, said pusher member being adapted to be engaged by said block during the expansion thereof, and said deflecting element comprising a puller wire attached to said pusher member to move therewith, said puller wire being positioned so as to engage said fiber to pull the fiber along the longitudinal axis of the fiber and cause the fiber to bend into said cavity when the block of material expands.

10. An optical fiber sensor according to claim 9 wherein said pusher member is in engagement with said block of material in the absence of said particular gaseous or liquid substance in said chamber.

11. An optical fiber sensor according to claim 9 wherein said pusher member is spaced from said block of material by a predetermined amount in the absence of said particular gaseous or liquid substance in said chamber.

12. An optical fiber sensor for detecting the presence of a particular gaseous or liquid substance comprising means for providing a track for receiving an optical fiber along a predetermined path including a cavity therein to permit the fiber to be deflected out of said predetermined path, means defining a chamber spaced from said predetermined path, said chamber being provided with sufficient openings to permit the flow of said gaseous or liquid substance within said chamber, a block of expansible material positioned within said chamber with said material being subject to expansion in the presence of said particular gaseous or liquid substance, said chamber and block of material being relatively dimensioned so as to permit the expansion of the block of material in a particular direction within the chamber and a pusher member positioned to move with said block of material as it expands in said direction, said pusher member including a deflecting element arranged in contact with said fiber for causing said fiber to be deflected into said cavity when the block of material expands in the presence of said particular gaseous or liquid substance, said means for providing a track including a removable member for confining a segment of the fiber to a fixed location directly adjacent to said cavity and generally permitting only sliding movement of the fiber along the longitudinal axis of the fiber as the fiber is deflected into said cavity said removable member including means for permitting the rapid removal and replacement of the removable member so that the optical fiber may be readily inserted into or removed from the sensor without requiring the insertion of an end of the fiber along the track.

13. An optical fiber sensor according to claim 12 wherein said pusher member includes a stem positioned to move exteriorly of the sensor so as to provide a visual indicator of the presence of said particular gaseous or liquid substance in said chamber.

14. An optical fiber sensor according to claim 13 including means for preventing said stem from returning to its initial position in said sensor so that said visual indicator remains even after the expansible block shrinks as the particular gaseous or liquid substance departs therefrom.

15. An optical fiber sensor according to claim 13 including means for adhesively securing the stem within said sensor, said adhesive securing means being overcome by the force of said means pusher member when said block of material expands.

16. An optical fiber sensor according to claim 12 wherein said means for permitting rapid removal and replacement of the removable member comprises a snap-fit connection between the removable member and the means for providing a track.

17. An optical fiber sensor for detecting the presence of free water and for distinguishing it from water vapor comprising means for providing a track for receiving an optical fiber along a predetermined path including a cavity therein to permit the fiber to be deflected out of said predetermined path, means defining a chamber spaced from said predetermined path, said chamber being provided with sufficient openings to permit the flow of water therein, a block of expansible material positioned within said chamber with said material being subject to expansion in the presence of water, a pusher member arranged to be moved within said chamber by the force exerted by the expansion of said block of material, said pusher member including a deflector element arranged in contact with said fiber for causing said fiber to be deflected into said cavity when the pusher member is moved, and means for preventing the expansion of the material from exerting a force on the pusher member which will cause it to move in the presence of water vapor alone within the chamber but permitting the movement of the pusher member by the expanding block of material in the presence of free water within the chamber.

18. An optical fiber sensor according to claim 17 wherein said means for providing a track and said deflector element provide three spaced support surfaces of curvilinear shape for the fiber adjacent said cavity with each of such surfaces being provided with a carefully controlled geometry so that the fiber will be bent in a predetermined manner for a given length of movement of the deflector element.

19. An optical fiber sensor according to claim 17 wherein said means for preventing comprises the initial spacing of the pusher member from the block of material by a predetermined distance so that the presence of water vapor within the chamber will only permit the expansion of the block of material to a distance less than said predetermined distance.

20. An optical fiber sensor according to claim 17 wherein said chamber has two ends with said block being fixed in position substantially at one end of the chamber and being expandable in the presence of water or water vapor into the other end of the chamber, said pusher member being located in said other end of the chamber.

21. An optical fiber sensor according to claim 17 including means for preventing the pusher member from returning to its initial position in the chamber after it has been moved therefrom by the expansion of the block of expansible material even during subsequent contraction of the block.

* * * * *